United States Patent [19]

Brack

[11] Patent Number: 5,135,754
[45] Date of Patent: Aug. 4, 1992

[54] METHOD OF PREPARING A COPOLYMER OF TWO α-AMINO ACIDS AND A COPOLYMER THUS OBTAINED

[75] Inventor: André E. Brack, Olivet, France

[73] Assignee: Delalande S.A., Courbevoie, France

[21] Appl. No.: 657,249

[22] Filed: Feb. 15, 1991

Related U.S. Application Data

[62] Division of Ser. No. 289,902, Dec. 23, 1988, abandoned.

Foreign Application Priority Data

Jan. 6, 1988 [FR] France .................. 88 00064

[51] Int. Cl.$^5$ ............................................. A61F 13/00
[52] U.S. Cl. ................................. 424/443; 523/111; 528/313
[58] Field of Search .................. 428/310.5; 514/202; 528/313; 424/443

[56] References Cited

U.S. PATENT DOCUMENTS

| | | | |
|---|---|---|---|
| 2,699,391 | 1/1955 | Mueller | 95/7 |
| 2,993,053 | 7/1961 | Ballard | 260/307 |
| 2,996,513 | 8/1961 | Ballard | 260/307 |
| 3,637,727 | 1/1972 | Fujimoto et al. | 260/307 |
| 3,644,412 | 2/1972 | Fujimoto et al. | 260/307 |
| 3,867,520 | 2/1975 | Mori et al. | 528/327 |
| 4,125,519 | 11/1978 | Goodman et al. | 528/327 |
| 4,161,948 | 7/1979 | Bichon | 428/310.5 |
| 4,374,134 | 2/1983 | Kocsis | 514/202 |

FOREIGN PATENT DOCUMENTS

| | | | |
|---|---|---|---|
| 653597 | 5/1951 | United Kingdom | 528/327 |
| 675298 | 7/1952 | United Kingdom | 528/327 |

*Primary Examiner*—Thurman K. Page
*Assistant Examiner*—William E. Benston
*Attorney, Agent, or Firm*—Flynn, Thiel, Boutell & Tanis

[57] ABSTRACT

The invention provides a method of synthesizing a copolymer of two α-amino acids which comprises the preparation of an N-carboxyanhydride of a first α-amino acid and the N-carboxyanhydride of a second α-amino acid, followed by the copolymerization of this mixture. The mixture is obtained by the reaction of phosgene with a mixture of a first and the second α-amino acids, the amino acids having similar reaction rates with phosgene. It also relates to the copolymer obtained by implementation of this method and an agent for covering skin wounds comprising this copolymer.

10 Claims, No Drawings

METHOD OF PREPARING A COPOLYMER OF TWO α-AMINO ACIDS AND A COPOLYMER THUS OBTAINED

This application is a division of U.S. Ser. No. 07/289,902, filed Dec. 23, 1988, now abandoned.

The present invention relates to a new method of synthesizing a copolymer of two α-amino acids, which comprises the preparation of a mixture of a N-carboxyanhydride of a first α-amino acid and a N-carboxyanhydride of a second α-amino acid, followed by the copolymerization of this mixture. It also relates to the copolymer obtained using this method.

In known methods of this type, the mixture of the N-carboxyanhydride of the first and second α-amino acids is obtained (i) by preparing separately the N-carboxyanhydride of the first α-amino acid and the N-carboxyanhydride of the second α-amino acid by separate reaction of the phosgene with the first amino acid and with the second amino acid, then (ii) by mixing, possibly after purification, the two N-carboxyanhydrides thus obtained. Because of the separate preparation of the two N-carboxyanhydrides, these known methods require the use of two parallel production lines, each comprising a reactor with different accessories (agitator, temperature measuring means, reflux device, intakes for the reagents, means for adjusting the phosgene flowrate, means for discharging the reaction mixture), means for purifying the N-carboxyanhydride and means for transferring said N-carboxyanhydride to the copolymerization reactor. The use of these methods requires then necessarily complex and therefore costly equipment. Furthermore, it is often difficult to program all the operations carried out with this equipment for there to be synchronism between the two parallel production lines. Such a difficulty results not only from the complexity of the equipment used but also from the fact that the reaction of one of the α-amino acids with the phosgene may require a longer time than the other α-amino acid. It thus often happens, with the above described known methods that the operations relative to one of the N-carboxyanhydrides are finished before those relative to the other N-carboxyanhydride, so that the N-carboxyanhydride obtained first must be stored for a period of time before being used for copolymerization. Now, it has been observed that these N-carboxyanhydrides do not keep well and are sensitive to different agents, particularly humidity, which means that precautions must be taken which further complicate the equipment and the synthesis of said N-carboxyanhydrides.

The purpose of the present invention is to overcome the above drawbacks and, for this, provides a method according to the one defined in the first paragraph of this description which is characterized in that the mixture of the N-carboxyanhydrides of the first and second α-amino acids is obtained by action of the phosgene on a mixture of a first and a second α-amino acid which have similar reaction rates with the phosgene. It will in fact be understood that by appropriately selecting the starting α-amino acids, namely those having similar reaction rates with phosgene, it becomes possible to react them simultaneously with the phosgene in a single reactor and a single production line is then sufficient for obtaining the desired N-carboxyanhydrides this not only greatly simplifies the equipment to be provided for synthesis of the desired copolymer but further avoids any risk of degradation of the N-carboxyanhydrides since they are obtained simultaneously and the temporary storage of one or the other is no longer necessary.

The first and second α-amino acids advantageously have a carbon atom in position β in the form $CH_2$ and an α amino group in the form $NH_2$. It is particularly preferable for one of the acids to be formed by leucine, particularly L-leucine, and for the other acid to be formed by glutamic acid or glutamic acid whose carboxyl function the furthest away from the amine function is esterified by a methyl or benzyl group, particularly L-glutamic acid or the methylic or benzylic ester of L-glutamic acid.

The mixture of the first and second α-amino acids to be reacted with the phosgene advantageously comprises from 40 to 60 mole % of one of these amino acids and 60 to 40 mole % of the other.

The reaction of the α-amino acids may be carried out in an organic solvent and dioxane or tetrahydrofurane may be mentioned by way of examples.

Before copolymerization of the resultant N-carboxyanhydrides, it is desirable to subject them to an appropriate treatment for reducing their chlorinated derivative content, preferably to a value less than 0.1%, these derivatives being produced during the reaction of the phosgene with the α-amino acids. Such treatment is described hereafter within the disclosure of preparations illustrating the present invention.

The mixture of the N-carboxyanhydrides is then subjected to the copolymerization reaction, advantageously at moderate temperatures, in an appropriate solvent such as dioxane and in the presence of a copolymerization initiator such as a tertiary amine (triethylamine, tributylamine, triethanolamine etc.), possibly in the presence of a lithium salt (chloride or nitrate for example) or a strong base such as an alkaline metal alcoholate (sodium methoxide for example). The ratio of the sum of the number of moles of the N-carboxyanhydrides to the number of moles of the copolymerization initiator depends on the initiator used and on the viscosity desired for the copolymer. Thus, in the case where the initiator is formed by tributylamine, a ratio in the range from 25 to 200 fields a copolymer having an intrinsic viscosity appropriate for the uses described hereafter for which this copolymer is intended. Similarly, when the initiator is sodium methoxide, a ratio in the range from 100 to 1000 gives an appropriate copolymer.

The copolymer obtained with the above method is isolated by introducing the reaction mixture into a great excess of water. By proceeding thus, the copolymer precipitates in the form of a very hydrophobic and very bulky fibrous product.

This copolymer finds essentially its application as a means for covering skin wounds, skin zones being repaired, burns and zones from which grafts have been taken, which covering means promotes cicatrization, while ensuring, until healing or cicatrization has taken place, the protection of these wounds and zones against external aggressions, whether they be of a mechanical or microbial kind.

With a view to this use, the copolymer is applied in a form appropriate to its application in a thin layer on the part to be protected. Thus, this copolymer may for example be applied in the form of a thin film or a powder or incorporated in a gel. From this copolymer a thin film may more particularly be formed using the well known technique of phase inversion as will be described hereafter in greater detail. Such a film is generally translucent, flexible and non porous, it has a thickness preferably between 300 and 750 μm and it is permeable to oxygen, to water vapour and to certain disinfectant solutions which it might possibly be desirable to apply through this film. To obtain a film with these characteristics, it is desirable for the copolymer to have an intrinsic viscosity at 30° C. in dichloroacetic acid between 0.5 and 3 dl/g. After healing or cicatrization, the film, the powder or the gel is removed or is spontaneously eliminated from the zone on which it was applied.

The following preparations are given by way of illustration of the invention.

Preparation of methyl L-glutamate (L-Glu(OMe))

1.25 liter of methanol is placed in a 2 liter reactor. 100 ml of acetyl chloride is then poured in at a temperature less than 20° C. With the pouring finished and under the same temperature conditions, 148 g of L-glutamic acid is added and the mixture is agitated at ambient temperature for 24 hours. Then 125 ml of pyridine is poured into the mixture obtained at a temperature less than 20° C. A precipitate forms and agitation is again carried out for 48 hours at ambient temperature. The precipitate is separated by filtration, washed twice with ethanol and once with ether, and then dried in a vacuum to give 174 g (yield: 86.56%) of the expected ester, which is in the form of a white powder.

|    | Elementary analysis | |
|----|-----------|----------------|
|    | Found (%) | Calculated (%) |
| C: | 45.22–45.23 | 44.72 |
| H: | 7.14–7.16 | 6.88 |
| N: | 8.46–8.46 | 8.69 |

TLC:eluant:BuOH/CH$_3$COOH/H$_2$O: 4/1/1

Preparation of the mixture of the N-carboxyanhydrides of L-leucine and methyl L-glutamate 65.5 g of L-leucine (0.5 mole), 80.5 g of methyl L-glutamate (0.5 mole) and 1600 ml of anhydrous dioxane, passed previously over alumina to free it of the peroxides which it may contain, are placed in a 2 liter reactor having a 2 liter non return system, a gas intake permitting a high phosgene and argon flow, a ball refrigerant, a NaOH receiver and an active carbon column.

The suspension obtained is purged with argon for 30 mins. Then a rapid flow of phosgene is passed through the gas intake while stirring the mixture energetically. The temperature inside the reactor is brought to 40° C. After six hours, the reaction mixture becomes homogeneous. The solution is then swept with argon for at least 48 hours at 40° C. so as to eliminate a maximum of the chlorinated derivatives dissolved in the solution. Then, the solution is evaporated in a vacuum and the residue is exhausted with 20 liters of anhydrous dioxane per 2 liter portions. It is verified that the amount of chlorinated derivatives in the distillate decreases progressively.

The solution in the dioxane is evaporated in a vacuum and the residue is taken up with 800 ml of dry hexane. There is crystallization of a product on which, after vacuum drying, a potentiometric quantity determination of the chloride ions is carried out. In the case where the chloride ion content is greater than 0.4%, the dioxane exhaustion should be taken up again. In the opposite case, a final treatment with the theoretical amount of Ag$_2$O in solution in the dioxane should lower the chloride ion content to less than 0.1%. This is the condition required for obtaining, in the following step, a copolymer suitable for the formation of a thin film. About 140 g (yield 81.39%) of the expected mixture ready for copolymerization is finally obtained.

Preparation of the L-leucine and methyl L-glutamate copolymer 137 g of the mixture prepared as described above and 2000 ml of anhydrous dioxane are introduced into a 2 liter reactor having a powerful agitator. The obtained solution is brought, in an argon atmosphere, to a temperature of 40° C. Then, 16 ml of a 0.1M solution of sodium methoxide in dioxane or 8 ml of a 1M solution of tributylamine in dioxane is continuously introduced. After 4 hours agitation, the polymerization reaction starts and the solution becomes more and more viscous. It is left under agitation for 3 days while checking the disappearance of the characteristic band of the N-carboxyanhydrides at 1785 cm$^{-1}$ in IR. The polymerization time depends on the amount of chlorinated derivatives present in the medium and the amount of polymerization initiator used. For a chlorinated derivative content less than 0.1%, the mole ratio of the N-carboxyanhydride mixture to the initiator should be 100 when using tributylamine, or 500 when using sodium methoxide, is particularly suitable for obtaining a copolymer which can be formed into a film.

The viscous solution of the copolymer in the dioxane is then poured slowly into a container containing 10 liters of water. The copolymer precipitates from contact with the water, the precipitate is separated by filtration, it is dried in air on paper and the drying is finished in a vacuum. Thus, 85 g of a white product is obtained having the following characteristics:

intrinsic viscosity at 30° C. in dichloroacetic acid: 1.79 dl/g

|    | elementary analysis: | |
|----|-----------|----------------|
|    | Found (%) | Calculated (%) |
| C: | 56.04–56.17 | 56.23 |
| N: | 7.99–7.96 | 7.83 |
| N: | 10.48–10.42 | 10.93 |

(The percentages calculated are determined for an equimolar amount of L-leucine and methyl L-glutamate).

rotatory power: α = −44° (c = 1% in dichloroacetic acid) at 20° C. for the D spectral ray of sodium.

High pressure liquid chromatography: amount of L-leucine and L-glutamic acid after 48 hours hydrolysis in concentrated HCl at 100° C.:

L-leucine: 44%
L-glutamic acid: 56%

Manufacture of a thin film from the L-leucine and methyl L-glutamate copolymer

A collodion of the copolymer is first formed in a very polar organic solvent such as N-methyl pyrrolidone, N-dimethylacetamide, N-dimethylformamide, dimethylsulfoxide or difluoro- or trifluoroacetic acid. After pouring the obtained collodion, to the desired thickness (500 μm for example), on a glass plate, the plate supporting the copolymer is immersed in several successive water baths to coagulate the collodion and wash the resulting film. This film is removed from the glass plate and it is immersed in a bath containing 75% of PEG 600 and 25% of physiological serum so as to impregnate the film with it for conservation thereof. After being placed in an impermeable bag, it is sterilized by gamma ray radiation.

I claim:

1. A method for synthesizing a copolymer of a first α-amino carboxylic acid and a second α-amino carboxylic acid comprising the steps of: forming a mixture of said first and second α-amino carboxylic acids, the molar ratio of the first α-amino carboxylic acid to the second α-amino carboxylic acid in said mixture being from 40/60 to 60/40; reacting said mixture with phosgene to form a resultant mixture of an N-carboxyanhydride of the first α-amino carboxylic acid and an N-carboxyanhydride of the second α-amino carboxylic acid; reducing the chloride ion content of said resultant mixture to less than 0.1%; and polymerizing the treated resultant mixture to form said copolymer of said first and second α-amino carboxylic acids.

2. Method according to claim 1, characterized in that the first and second α-amino acids have a $CH_2$ group at the β-carbon atom and an $NH_2$ attached to the α-carbon atom.

3. Method according to claim 1, characterized in that one of the α-amino acids is leucine.

4. Method according to claim 1, characterized in that one of the α-amino acids is selected from the group consisting of glutamic acid, methyl glutamic acid ester and benzyl glutamic acid ester.

5. The method of claim 1, wherein said first and second α-amino carboxylic acids have similar rates of reaction with said phosgene.

6. A copolymer obtained by the method of claim 1, said copolymer having an intrinsic viscosity of from 0.5 to 3 dl/g as measured at 30° C. in dichloroacetic acid.

7. In a medical dressing for promoting cicatrization of skin wounds, skin zones undergoing healing, burns and skin zones from which skin grafts have been taken, the improvement comprising said medical dressing containing a copolymer of a first α-amino carboxylic acid and a second α-amino carboxylic acid, said first and second α-amino carboxylic acids having similar reaction rates with phosgene, said first α-amino carboxylic acid and said second α-amino carboxylic acid being present in said copolymer in a molar ratio of from 40/60 to 60/40 and said copolymer having an intrinsic viscosity of from 0.5 to 3 dl/g as measured at 30° C. in dichloroacetic acid.

8. In a method of promoting cicatrization of skin wounds, skin zones undergoing healing, burns and skin zones from which skin grafts have been taken, the improvement comprising utilizing a medical dressing containing a copolymer of a first α-amino carboxylic acid and a second α-amino carboxylic acid, said first and second α-amino carboxylic acids having similar reaction rates with phosgene, said first α-amino carboxylic acid and said second α-amino carboxylic acid being present in said copolymer in a molar ratio of from 40/60 to 60/40 and said copolymer having an intrinsic viscosity of from 0.5 to 3 dl/g as measured at 30° C. in dichloroacetic acid.

9. The medical dressing of claim 7, wherein said copolymer is obtained from a mixture of an N-carboxyanhydride of the first α-amino carboxylic acid and an N-carboxyanhydride of the second α-amino carboxylic acid, said mixture having a chloride ion content of less than 0.1%.

10. The method of claim 8, wherein said copolymer is obtained from a mixture of an N-carboxyanhydride of the first α-amino carboxylic acid and an N-carboxyanhydride of the second α-amino carboxylic acid, said mixture having a chloride ion content of less than 0.1%.

* * * * *

UNITED STATES PATENT AND TRADEMARK OFFICE
CERTIFICATE OF CORRECTION

PATENT NO. : 5 135 754
DATED : August 4, 1992
INVENTOR(S) : André E. Brack

It is certified that error appears in the above-identified patent and that said Letters Patent is hereby corrected as shown below:

ON THE TITLE PAGE:

Under ABSTRACT, Section [57], Line 7; change
"mixture of a first and the second" to
---mixture of the first and a second---.

Column 5, Line 34; change "30°C." to ---"30°C"---.

Column 6, Line 10; change "30°C." to ---"30°C"---.

Column 6, Line 23; change "30°C." to ---"30°C"---.

Signed and Sealed this

Twelfth Day of October, 1993

Attest:

BRUCE LEHMAN

*Attesting Officer*        *Commissioner of Patents and Trademarks*